(12) United States Patent
Gloor (10) Patent No.: US 7,670,800 B2
(45) Date of Patent: Mar. 2, 2010

(54) PROCESS FOR THE PURIFICATION OF RIBOFLAVIN

(75) Inventor: Arnold Gloor, Oberwil (CH)

(73) Assignee: DSM IP Assets B.V., Te Heerlen (NL)

( * ) Notice: Subject to any disclaimer, the term of this patent is extended or adjusted under 35 U.S.C. 154(b) by 257 days.

(21) Appl. No.: 10/565,443

(22) PCT Filed: Jul. 20, 2004

(86) PCT No.: PCT/EP2004/008097

§ 371 (c)(1),
(2), (4) Date: May 12, 2006

(87) PCT Pub. No.: WO2005/014594

PCT Pub. Date: Feb. 17, 2005

(65) Prior Publication Data

US 2006/0240112 A1    Oct. 26, 2006

(30) Foreign Application Priority Data

Jul. 22, 2003   (EP) .................................. 03016512

(51) Int. Cl.
*C12P 25/00* (2006.01)
(52) U.S. Cl. .................. 435/66; 435/262; 544/251
(58) Field of Classification Search ...................... None
See application file for complete search history.

(56) References Cited

U.S. PATENT DOCUMENTS

| 2,324,800 | A | 7/1943 | Pasternak et al. |
| 2,367,646 | A | 1/1945 | McMillan |
| 2,603,633 | A | 7/1952 | Dale |
| 2,797,215 | A | 6/1957 | Dale |
| 4,687,847 | A | 8/1987 | Grimmer et al. |
| 6,150,364 | A | 11/2000 | Wagner |

FOREIGN PATENT DOCUMENTS

| DE | 2 920 592 | 12/1980 |
| EP | 0 464 582 | 1/1992 |
| EP | 438 767 | 7/1995 |
| EP | 0 730 034 | 9/1996 |
| EP | 995 749 | 4/2000 |
| EP | 1 048 668 | 11/2000 |

OTHER PUBLICATIONS

Derwent Database English language abstract of EP (document B1 above).
Bezanilla, M. et al., "Adsorption of DNA to Mica, Silylated Mica, and Minerals: Characterization by Atomic Force Microscopy", Langmuir, 1995, vol. 11, pp. 655-659.
Khanna, M. et al., "X-ray diffractometry and electron microscopy of DNA from *Bacillus subtilis* bound on clay minerals", Sciences of Soils, 1998, 3:1.
Lindahl, T. et al., "Rate of Depurination of Native Deoxiribonucleic Acid", Biochemistry, 11, 19 (1972), pp. 3610-3618.
Van Loon, R.P.G.M. et al., "Development of a Fermentation Process for the Manufacture of riboflavin", Chimia 50, (1996), No. 9, pp. 410-412.

*Primary Examiner*—Herbert J. Lilling
(74) *Attorney, Agent, or Firm*—Hoxie & Associates LLC (57) ABSTRACT

The invention relates to a process for the purification of riboflavin comprising the steps of (a) precipitating a first crystalline form of riboflavin, (b) isolating the first crystalline form of riboflavin, (c) transforming the first crystalline form of riboflavin into a second crystalline form of riboflavin under conditions that decompose diluted DNA, and (d) isolating the second crystalline form of riboflavin, provided that at ambient temperature the first crystalline form of riboflavin is thermodynamically less stable than the second crystalline form of riboflavin.

11 Claims, 10 Drawing Sheets

Fig. B: Anhydrate II

Fig. C: Anhydrate III

Fig. D: Monohydrate

Fig. E: Dihydrate

Fig. F: Tetrahydrate

Fig. 1: Solubility lines of crystalline forms of Riboflavin

Fig. 3: DVS: Anhydrate II – Monohydrate – Dihydrate

Fig. 4: DVS: Anhydrate III - Tetrahydrate

Fig. 5

Target DNA: 200 base pair of a production strain DNA amplified by 45 cycles.

1  2  3  4  5  6  7  8  9  10  11  12  13  14  15  16  P  N  Trace

←signal, target DNA
←primer dimers

Results of the amplification reaction with two primers.

Trace P: Positive control
Trace N: Negative control
Trace 6: Trace of the sample prepared in example 3. No DNA was amplified: The primer dimers were amplified during the reaction in the absence of target DNA.

PROCESS FOR THE PURIFICATION OF RIBOFLAVIN

The invention relates to a process for the purification of riboflavin (vitamin $B_2$), which process is particularly suitable for the removal of DNA associated with riboflavin crystals.

While riboflavin has been produced synthetically in the past, modern processes for the production of riboflavin are based on fermentation technology for economical reasons. Such processes have in common that riboflavin is produced by microorganisms and the pure product is obtained by consecutive purification steps starting from the crude reaction slurry (fermentation broth) containing the riboflavin.

Fermentation processes for the production of riboflavin are known from the prior art. In this regard it can be referred to e.g. Takata, Ryohei; Nagata, Toshiomi; Shimamoto, Sumio; Solubility of riboflavin obtained from cultured *Eremothecium ashbyii* (1949) 27, pp. 8-10 and 50-52; Sen Gupta, S. B.; Gupta, H. N.; Solubility of riboflavin (vitamin B2) in water; J. Proc. Inst. Chemists (India) (1949) 21, pp. 1-4; Chemical Engineering, April 2002, p. 23; van Loon R. P. G. M. et al.; Development of a Fermentation Process for the Manufacture of riboflavin; Chimia 50 (1996) No. 9 pp. 410-412; EP-A 428 767; EP-A 464 582 and DE-A 2 920 592.

In the course of the fermentation process the concentration of the riboflavin in the fermenter steadily increases. However, the solubility of riboflavin in aqueous solutions is rather poor; in neutral aqueous solutions and at a temperature of between 30° C. and 50° C. a solubility of about 0.014 wt.-% to 0.031 wt.-% has been reported. Therefore, when a certain level of supersaturation has been reached in the fermentation process, the riboflavin spontaneously starts to crystallize. Once the first crystallites have been formed during the fermentation process, the riboflavin produced by the proceeding fermentation continuously crystallizes until the fermentation process has finished.

In general, the reaction slurry (fermentation broth) containing the riboflavin crystals is transferred to the downstream part of the process. In a first step the reaction slurry is usually pasteurized, i.e. the microorganisms are killed under acidic conditions and at elevated temperatures. In a second step the major part of the biomass is removed from the reaction slurry by decantation. In a third step the reaction slurry is acidified and heated up to 95° C. to 115° C. in order to decompose and remove remaining impurities (e.g. biomass, proteins, lipids, DNA) to a certain extent, thereby purifying the riboflavin crystals. During the acid treatment the purity of the riboflavin crystals usually increases from about 85 wt.-% to about 96 wt.-%. In a fourth step the acidified reaction slurry is filtered and washed. Optional further steps include purification steps and/or formulation steps to obtain the final product form.

In the purification step (third step) lipids, proteins, DNA and other organic and inorganic compounds may be removed to a certain extent only. It has been reported that a purity of up to 97 wt.-% can be achieved by adding 2 wt.-% of sulfuric acid or another mineral acid and heating the reaction slurry to a temperature in the range of 95° C. to 105° C.

However, the quality of the riboflavin produced in the fermentation processes of the prior art is not satisfactory, as the product still contains a significant amount of impurities, particularly DNA. On the one hand the purity of the riboflavin should be as high as possible, in particular for pharmaceutical or nutritional purposes. On the other hand, however, the purification process should be rather simple, effective, quantitative and gentle (e.g. riboflavin should not be exposed to high temperatures for a certain period of time to prevent the formation of deteriorated products).

It is an object of the invention to provide a process for the purification of riboflavin which is superior over the processes of the prior art.

This underlying technical problem has been solved by the subject matter of the patent claims, i.e. by a process for the purification of riboflavin comprising the steps of
(a) precipitating a first crystalline form of riboflavin,
(b) isolating the first crystalline form of riboflavin,
(c) transforming the first crystalline form of riboflavin into a second crystalline form of riboflavin under conditions that decompose diluted DNA, and
(d) isolating the second crystalline form of riboflavin, provided that at ambient temperature the first crystalline form of riboflavin is thermodynamically less stable than the second crystalline form of riboflavin.

The term "ambient temperature" means average room temperature, preferably 23° C.

It has been surprisingly found that by said process the DNA content of the riboflavin crystals can be significantly reduced, i.e. preferably to an extent which is below the detection limit of conventional PCR analysis (approximately 0.2 ppb).

Said purification process of riboflavin can be conducted under conditions (temperature, residence time, acid concentration, etc.) which are by far more gentle than the conditions of the processes of the prior art not transforming a first crystalline form of riboflavin into a second crystalline form of riboflavin.

The invention is based on the unexpected finding that, depending on the conditions in the fermenter, the crystallization of riboflavin during fermentation leads to different crystalline forms (modifications). The analysis of the riboflavin crystals in the fermentation broth revealed that in some batches an anhydrate (i.e. riboflavin anhydrate I) and in other batches a hydrate (i.e. riboflavin dihydrate) was precipitated. In other batches mixtures of both crystalline forms were found. Even a third crystalline form (i.e. riboflavin tetrahydrate) was identified in some cases. These crystalline forms, i.e. riboflavin hydrates and riboflavin anhydrates were characterized by X-ray powder diffraction (XRD) and Dynamic Vapor Sorption (DVS). The solubilities of the different crystalline forms were investigated by Raman spectroscopy. The combination of DVS with XRD allows to investigate the formation of the hydrates.

It has been found that three different anhydrous crystalline modifications (riboflavin anhydrates I, II and III) are in equilibrium with different riboflavin hydrates (riboflavin monohydrate, dihydrate and tetrahydrate).

Depending on the temperature the following crystalline forms are in equilibrium with one another or are irreversibly transformed into each other under defined conditions (e.g. temperature, humidity, etc.):

riboflavin anhydrate I with riboflavin dihydrate and riboflavin tetrahydrate; riboflavin anhydrate II with riboflavin monohydrate and riboflavin dihydrate; riboflavin anhydrate III with riboflavin tetrahydrate.

At 23° C. the situation regarding riboflavin anhydrate I and riboflavin dihydrate can be illustrated as follows:

At 23° C. the equilibrium between riboflavin anhydrate I and riboflavin dihydrate is completely shifted to the side of riboflavin anhydrate I, i.e. at this temperature riboflavin dihydrate is irreversibly transformed into riboflavin anhydrate I. Thus, at 23° C. no riboflavin dihydrate can be obtained from pure riboflavin anhydrate I. Also at higher temperatures, e.g. at 39° C., riboflavin dihydrate is thermodynamically less stable than riboflavin anhydrate I.

At 23° C. the kinetic of the transformation of riboflavin dihydrate into riboflavin anhydrate I is rather slow. Stirring a slurry containing pure riboflavin dihydrate at a temperature of 23° C. results in a partial transformation (80%) into riboflavin anhydrate I in 11 days (determined by Raman spectroscopy). At 39° C. the differences of the solubilities or the chemical potentials are small. Therefore, at this temperature the transformation of riboflavin dihydrate to riboflavin anhydrate I is slow.

At higher temperatures, the difference between the chemical potentials of riboflavin anhydrate I and riboflavin dihydrate increases. Therefore, the velocity of the transformation process significantly increases, as riboflavin dihydrate is completely transformed into riboflavin anhydrate I within 20 seconds at 80° C.

However, at 4° C. the thermodynamic situation is different. In an aqueous slurry riboflavin anhydrate I can be transformed into riboflavin dihydrate, the latter being irreversibly obtainable from riboflavin tetrahydrate (particularly at higher temperatures):

At 4° C. the kinetic of the transformation of riboflavin anhydrate I into riboflavin dihydrate is very slow. Stirring a slurry only containing riboflavin anhydrate I at a temperature of 4° C. leads to a partial transformation (80%) of riboflavin anhydrate I into riboflavin dihydrate in 56 days.

The investigation of the solubility of the crystalline forms, in particular of riboflavin anhydrate I, riboflavin dihydrate and riboflavin tetrahydrate, surprisingly revealed that below ca. 40° C. the solubility lines are very close to one another. At a certain temperature in the range between 4° C. and 23° C. the free Gibbs energy (ΔG) of the crystalline forms of riboflavin anhydrate I and riboflavin dihydrate are equal. At a certain temperature within said temperature range the solubility lines of riboflavin anhydrate I and riboflavin dihydrate intersect. At temperatures above the intersection riboflavin anhydrate I is thermodynamically the more stable crystalline form (lower free Gibbs energy); at temperatures below the intersection riboflavin dihydrate is thermodynamically the more stable crystalline form.

At 23° C. there is also an equilibrium between riboflavin anhydrate II with riboflavin monohydrate and riboflavin dihydrate, which equilibrium is dependent upon the relative humidity. Furthermore, also depending on the relative humidity, at 23° C. riboflavin anhydrate III can be reversibly transformed into riboflavin tetrahydrate:

The properties of the crystalline forms of riboflavin, in particular the solubility and the spontaneous crystallisation, have been carefully investigated (cf. Example 1). The results are summarized in FIGS. 1 and 2. Within the temperature range of 44° C. to 52° C. the solubility of riboflavin dihydrate and within the temperature range of 44° C. to 59° C. the spontaneous crystallization of riboflavin were investigated. Extrapolation of the supersaturation lines to 39° C. indicates that the supersaturation lines of riboflavin anhydrate I and riboflavin dihydrate approach each other rather closely. In another experiment riboflavin was dissolved at a concentration of 0.7 g l$^{-1}$ and at a temperature of 69° C.

Figure 1:
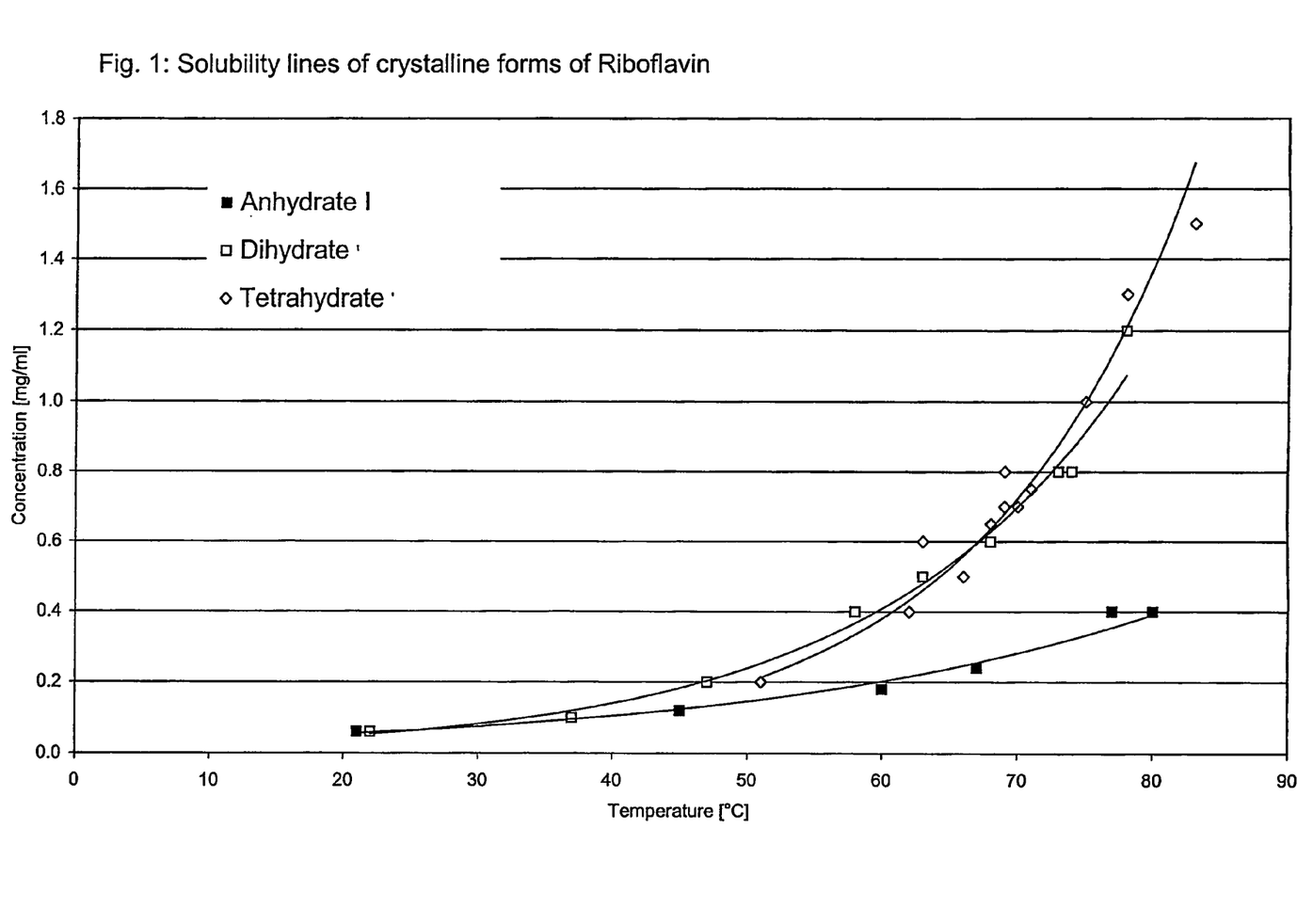
FIG. 1 illustrates the solubility lines of crystalline forms of riboflavin.
Figure 2:
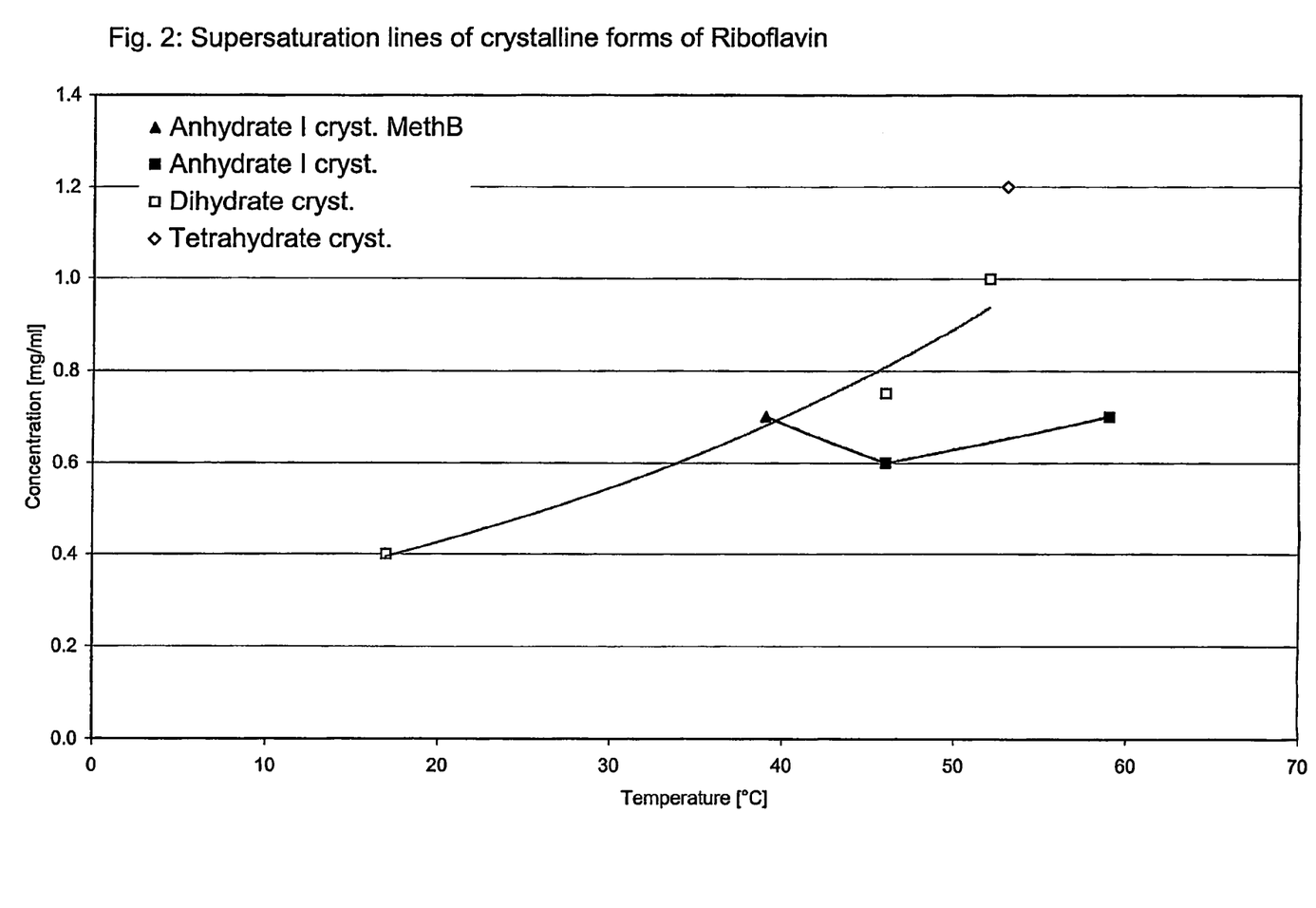
FIG. 2 illustrates the supersaturation lines of crystalline forms of riboflavin.

Continuous cooling of the solution to 39° C. within 3 h resulted in crystallization of riboflavin anhydrate I. At 39° C. riboflavin dihydrate is thermodynamically less stable than riboflavin anhydrate I. The position of the supersaturation line of riboflavin anhydrate I at 39° C. can be estimated to be above 0.6 g l$^{-1}$. Therefore, in the metastable zone between the supersaturation line and the solubility line it is possible to control the formation of the crystalline form of riboflavin by vaccination with seed crystals of the desired crystalline form.

BRIEF DESCRIPTION OF THE DRAWINGS

The powder diffractograms of the crystalline forms of riboflavin anhydrate I, riboflavin anhydrate II, riboflavin anhydrate III, riboflavin monohydrate, riboflavin dihydrate and riboflavin tetrahydrate are displayed in FIG. A-F. The intensity of the signal is shown on the y-axis; the scattering scale [theta] is depicted on the x-axis. According to IUPAC, the unit "theta" is defined as the angle between the forward direction of the incident beam and a straight line connecting the scattering point and the detector. FIGS. A through F each illustrates the X-ray diffraction of the different vitamin B$_2$ crystal modifications as follows.

FIG. A illustrates the X-ray diffraction of riboflavin Anhydrate I.

FIG. B illustrates the X-ray diffraction of riboflavin Anhydrate II.

FIG. C illustrates the X-ray diffraction of riboflavin Anhydrate III.

FIG. D illustrates the X-ray diffraction of riboflavin Monohydrate.

FIG. E illustrates the X-ray diffraction of riboflavin Dihydrate.

FIG. F illustrates the X-ray diffraction of riboflavin Tetrahydrate.

Regarding the terminology in the field of crystallography (e.g. the meaning of the terms "crystalline form", "polymorphism", "polymorph", etc.) it can be referred to e.g. Solid State Chemistry of Drugs; Stephen R. Byrn, Ralph R. Pfeiffer, Joseph G. Stowell: SSCI Inc. West Lafayette; 1999".

Anhydrates are crystalline forms that do not contain crystalline water, in particular under water free atmosphere. Riboflavin anhydrate I is a polymorph of riboflavin characterized by the X-ray diffractogram in FIG. A. Under water vapor riboflavin anhydrate II is in equilibrium with riboflavin monohydrate and riboflavin dihydrate. Under water vapor riboflavin anhydrate III is in equilibrium with riboflavin tetrahydrate.

Hydrates are crystalline forms containing crystalline water. Under water vapor riboflavin monohydrate (cf. FIG. D) is in equilibrium with riboflavin anhydrate II and riboflavin dihydrate. Riboflavin dihydrate is characterized by the X-ray diffractogram in FIG. E. Under water vapor riboflavin tetrahydrate (cf. FIG. F) is in equilibrium with riboflavin anhydrate III.

Various modifications of crystalline riboflavin are known from the prior art. In this regard it can be referred to e.g. EP-A 995 749, U.S. Pat. No. 2,324,800, U.S. Pat. No. 2,603,633, U.S. Pat. No. 2,797,215, U.S. Pat. No. 4,687,847 and International Center of Diffraction Data (2002 JCPDS; PCPDF-WIN v. 2.2; Data submitted by Eli Lilly and Company, Indiana, USA, 1955).

As in the prior art the nomenclature of the forms (modifications) of crystalline riboflavin is not unitary, the different terms are summarized in the table here below:

tated in form of crystalline riboflavin (first crystalline form of riboflavin) and only a comparably small amount of riboflavin remains in solution.

The process of the invention requires that at ambient temperature (preferably 23° C. or higher) the first crystalline form of riboflavin be thermodynamically less stable than the second crystalline form of riboflavin which is produced in step (c). This does not mean that step (a) itself has to be performed at ambient temperature, the temperature merely defines under which conditions the thermodynamic stability of the respective crystalline forms of riboflavin are to be compared. Preferably, step (a) is performed at a temperature of below 40° C.

On the one hand it has to be prevented that the crystalline form of riboflavin, which is precipitated in step (a), is thermodynamically the most stable form of crystalline riboflavin at ambient temperature, as in that case no transformation would be possible into any second crystalline form being thermodynamically more stable at ambient temperature. On the other hand the first crystalline form of riboflavin should be obtainable upon controlled precipitation and should stand the conditions of fermentation and an optional consecutive pasteurization step. Any crystalline form that exhibits these properties enables an efficient purification of riboflavin, particularly a significant decrease of the DNA concentration contained in the riboflavin crystals in step (c).

In a preferred embodiment of the process according to the invention the first crystalline form of riboflavin precipitated in step (a) comprises a riboflavin hydrate, preferably ribofla-

| nomenclature in this specification crystalline form of riboflavin | nomenclature of the prior art | | | | | |
|---|---|---|---|---|---|---|
| | EP-A 995 749 | U.S. Pat. No. 2,324,800 | U.S. Pat. No. 2,603,633 | U.S. Pat. No. 2,797,215 | U.S. Pat. No. 4,687,847 | FIG. |
| anhydrate I | modification A | =type A | type A | type A | =type A | A |
| anhydrate II | — | — | — | — | — | B |
| anhydrate III | — | — | — | — | — | C |
| monohydrate | modification B/C | — | — | — | — | D |
| dihydrate | — | — | — | — | — | E |
| tetrahydrate | — | — | type C | type C | — | F |
| anhydrate II + monohydrate | | | type B | type B | | |

In step (a) of the process according to the invention a first crystalline form of riboflavin is precipitated, i.e. crystallized. Preferably step (a) is performed starting from the crude reaction slurry produced by microorganisms in a fermenter (fermentation broth). Suitable microorganisms include non genetically modified organisms (non GMO) and genetically modified organisms (GMO). The fermentation process may be carried out continuously or as a batch process, the latter being preferred. Usually the amount of water contained in the fermenter is not sufficient to keep the entire amount of the riboflavin product dissolved. Thus, only the amount of riboflavin obtained in the very beginning of the fermentation process stays in solution, but in the course of the progressing fermentation, when a certain level of supersaturation has been reached, the riboflavin spontaneously starts to crystallize. In general, the crystallization initiates well in advance of the termination of the fermentation process. Therefore, at the end of the process the majority of the product has been precipivin monohydrate, riboflavin dihydrate or riboflavin tetrahydrate. Most preferably, the first crystalline form of riboflavin precipitated in step (a) is riboflavin dihydrate.

Depending on the reaction conditions in step (a), the first crystalline form of riboflavin which spontaneously precipitates from the fermentation broth is not necessarily the desired first crystalline form of riboflavin. Thus, it may become necessary to control the form of the precipitate of crystalline riboflavin which is precipitated in step (a), i.e. preferably produced in the course of the fermentation process.

It has been surprisingly found that in step (a) the formation of the desired first crystalline form of riboflavin in the fermenter can be controlled by initiation of the crystallization by means of seed crystals having a certain crystalline structure. The addition of suitable seed crystals to the fermentation broth causes the precipitation of a distinct first crystalline form of riboflavin. Therefore, the precipitation of the preferred first crystalline form of riboflavin (e.g. riboflavin monohydrate, riboflavin dihydrate or riboflavin tetrahydrate), preferably riboflavin dihydrate can be performed by means of selected suitable seed crystals.

The initiation of crystallization by means of seed crystals (vaccination) is a known technology whereby the form of the product to be crystallized can be influenced. In this regard it can be referred to e.g. Crystallization Technology Handbook; A. Mersmann; Marcel Decker, Inc.; 1995.

In a preferred embodiment of the process according to the invention the precipitation of the first crystalline form of riboflavin in step (a) is initiated by means of seed crystals, preferably by means of seed crystals of riboflavin. Preferably the seed crystals comprise seed crystals of a riboflavin hydrate, more preferably of riboflavin monohydrate, riboflavin dihydrate or riboflavin tetrahydrate. Most preferably the seed crystals of riboflavin comprise riboflavin monohydrate.

Preferably the first crystalline form of riboflavin precipitated in step (a) is riboflavin dihydrate or riboflavin tetrahydrate which is obtained by means of suitable seed crystals. Preferably the first crystalline form of riboflavin is riboflavin dihydrate the precipitation of which being preferably controlled by seed crystals of riboflavin monohydrate.

It has been surprisingly found that seed crystals of riboflavin monohydrate are suitable for the precipitation of riboflavin dihydrate. When crystals of riboflavin monohydrate are brought into contact with water, riboflavin dissolved in an supersaturated aqueous solution (fermentation broth) is immediately precipitated in the crystalline form of riboflavin dihydrate. The investigation of the nature of the crystalline forms revealed that in aqueous dispersions crystalline riboflavin monohydrate is rapidly transformed into crystalline riboflavin dihydrate.

In a preferred embodiment of the invention the seed crystals are added to the fermentation broth after 2 to 10 h, preferably after 4 to 7 h. Preferably the seed crystals are transferred into the fermenter from a sterile bottle by means of a needle.

A process for the preparation of crystalline riboflavin monohydrate is known from the prior art (cf. EP-A 995 749—modification B/C).

Crystalline riboflavin dihydrate can be produced by adding seed crystals of riboflavin monohydrate to a supersaturated aqueous solution of riboflavin, preferably at a pH value of 5-8, more preferably at a pH value of 6.5-7. One aspect of the invention is related to riboflavin dihydrate. Another aspect of the invention is related to a process for the preparation of crystalline riboflavin dihydrate wherein crystalline riboflavin monohydrate is added to a saturated aqueous solution of riboflavin.

Crystalline riboflavin tetrahydrate can be produced under vacuum by evaporating water from an aqueous solution of riboflavin at about 40° C. To obtain the starting material, i.e. the aqueous solution of riboflavin, preferably riboflavin anhydrate I is suspended in deionized water at a concentration of about 0.07 g $l^{-1}$ (cf. Example 6). The saturated solution can then be separated from the undissolved crystals by means of a filter system including a combination of a pre-filter with fiberglass and a 5 µm Teflon filter. The saturated aqueous solution of riboflavin is continuously added to the solution of riboflavin contained in the rotational evaporator. Simultaneously, the water is evaporated, preferably at a temperature of between 30 and 60° C., particularly between 35 and 45° C. and under a vacuum of 10 to 100 mbar, preferably of 20 to 25 mbar. Preferably the bath temperature should not exceed 40° C. The solution of the riboflavin is continuously transferred into the flask of the evaporator, while the volume of the solution in the flask is kept constant by evaporation. The crystallization initiates at a certain point. After the evaporation is terminated the slurry is filtered. The wet crystals of riboflavin tetrahydrate can be characterized by XRD. One aspect of the invention is related to riboflavin tetrahydrate. Another aspect of the invention is related to a process for the preparation of riboflavin tetrahydrate wherein water is evaporated from a solution of riboflavin at a temperature of about 40° C. under vacuum and a saturated solution of riboflavin is added to the rotating evaporator simultaneously.

The further processing to obtain suitable seed crystals of crystalline riboflavin monohydrate, dihydrate and tetrahydrate or other suitable crystalline forms of riboflavin useful in step (a) is described here below.

In step (a) of the process according to the invention a successful precipitation of the desired first crystalline form of riboflavin requires that the seed crystals be in the desired crystalline form, preferably riboflavin monohydrate, riboflavin dihydrate or riboflavin tetrahydrate, more preferably riboflavin monohydrate or riboflavin dihydrate. Furthermore, the seed crystals should be sterile not to contaminate the fermentation process by organisms from outside.

The seed crystals of riboflavin can be prepared in seed fermenters or in another suitable reactor. The riboflavin which is introduced as the starting material into the seed fermenters has to be fully diluted. Any impurity, i.e. any undissolved crystal of an undesired crystalline form, later in step (a) of the process will usually result in the precipitation of the identical undesired crystalline form thereby yielding an undesired intermediate (i.e. the first crystalline form of riboflavin). In particular, any impurity of riboflavin anhydrate I in the seed crystals inevitably results in the precipitation of riboflavin anhydrate I during the fermentation process and hence is to be avoided.

In a preferred embodiment of the invention the seed crystals of riboflavin are in the form of riboflavin monohydrate. The preparation preferably starts from riboflavin monohydrate (cf. EP-A 995 749). The crystals of riboflavin monohydrate then are suspended in water at a temperature ranging from 2° C. to 40° C., preferably 10° C. to 20° C. and under these conditions riboflavin monohydrate is transformed into riboflavin dihydrate. The crystals are filtered off and dried in order to remove the surface water. Grinding of the crystals increases the specific surface that later in step (a) leads to a higher nucleation rate after introduction into the fermentation broth. The milled crystals are then washed with pure ethanol or a mixture of ethanol and water.

Preferably the seed crystals of riboflavin are sterilized before they are used in step (a) of the process according to the invention. Preferably the seed crystals are sterilized upon steam sterilization or by a solvent, preferably a mixture of ethanol and water, most preferably a mixture of >70% ethanol and water.

In case that the seed crystals are sterilized by steam, the dry crystals of riboflavin monohydrate or riboflavin dihydrate are transferred into a closed system. In this system the crystals are heated to temperatures of between 110° C. and 150° C., preferably between 120° C. and 140° C., preferably for about 30 min. In a preferred embodiment of the process according to the invention seed crystals of a riboflavin hydrate, more preferably of riboflavin monohydrate or riboflavin dihydrate are sterilized by steam and temperature, preferably at 120-140° C. It has been surprisingly found that under these conditions the crystalline form of the seed crystals does not change.

Another possibility is the sterilization by a solvent. A second sterilization procedure can be performed by the addition of a solvent, e.g. of an alcohol or a ketone, whereby the addition of ethanol or methanol is preferred. As the seed crystals of riboflavin are practically insoluble in the solvent, a slurry is formed from which the solvent is then filtered off. The wet crystals are washed with sterilized water to remove the remainder of the solvent. In a preferred embodiment of the process according to the invention seed crystals of a riboflavin hydrate, more preferably of riboflavin monohydrate or riboflavin dihydrate are sterilized by a mixture of ethanol and water, preferably containing 70 vol.-% to 90 vol.-% of ethanol. It has been surprisingly found that under these conditions the crystalline form of the seed crystals does not change.

At this moment the freshly prepared seed crystals of riboflavin are ready for use in step (a) of the process according to the invention. XRD shows that after sterilization the crystalline form does not change. It has been surprisingly found that the sterilized seed crystals are stable at room temperature in a solution that contains 80% alcohol and 20% water. However, a higher alcohol concentration leads to a change of the crystalline form.

In a preferred embodiment of the process according to the invention steam sterilization and sterilization by a solvent are combined. Preferably the seed crystals are sterilized by steam at a temperature above 100° C., preferably at about 140° C. for about 50 min in an oven. Then, the seed crystals are suspended in 0-1000 weight equivalents, preferably 5-100 weight equivalents of ethanol for 10 to 200 min, preferably for 20 to 40 min. Prior to use in step (a), preferably 0-100 volume equivalents of sterile $H_2O$ are added for better handling of the liquid.

In a preferred embodiment of the process according to the invention the seed crystals comprise a riboflavin hydrate, particularly riboflavin monohydrate or riboflavin dihydrate. Preferably the seed crystals are added to the fermentation broth in step (a) when the concentration of the diluted riboflavin exceeds the solubility limit of the better soluble crystalline form, which (depending on the temperature) may be riboflavin dihydrate. Above the solubility limit of riboflavin dihydrate and riboflavin anhydrate I, there is a metastable zone of riboflavin anhydrate I.

Spontaneous crystallization of the riboflavin anhydrate I does not occur. Preferably, the vaccination occurs at temperatures between 36° C. and 43° C. and at a riboflavin concentration of 0.16 g $l^{-1}$ to 0.23 g $l^{-1}$ in the fermentation broth.

In step (b) of the process according to the invention the first crystalline form of riboflavin is isolated. This means that, when step (a) has been performed starting from the crude reaction slurry contained in a fermenter, preferably the major part of the biomass is removed from the reaction slurry. Preferably the first crystalline form of riboflavin is isolated by decantation, i.e. by separation of the overhead from the precipitate (biomass separation). Step (b) of the process according to the invention usually does not result in an isolation of pure riboflavin. In general, the isolated first crystalline form of riboflavin still contains impurities which have to be separated in further purification steps. The invention is particularly concerned with the removal of these impurities.

In a preferred embodiment of the process according to the invention the first crystalline form of riboflavin precipitated in step (a) and isolated in step (b) is pasteurized, preferably after step (b) but preferably prior to step (c). Preferably the pasteurization is performed by heating the first crystalline form of riboflavin which was separated from the major amount of biomass contained in the reaction slurry earlier in step (b). In a preferred embodiment the pasteurization is performed at a temperature ranging from 40° C. to 80° C., preferably from 60° C. to 75° C. Preferably the pasteurization is performed under acidic conditions. The pasteurization is preferably performed at a pH value of below 6, more preferably at a pH value of below 4. Preferred acids which may be added to an aqueous suspension of the first crystalline form of riboflavin are mineral acids, preferably sulfuric acid or nitric acid, or organic acids, preferably carboxylic acids, most preferably formic acid or oxalic acid.

In step (c) of the process according to the invention the first crystalline form of riboflavin is transformed into a second crystalline form of riboflavin under conditions that decompose diluted DNA. It is an essential feature of the process according to the invention that at ambient temperature (preferably 23° C.) the first crystalline form of riboflavin is thermodynamically less stable than the second crystalline form of riboflavin. Preferably, the first crystalline form of riboflavin is thermodynamically less stable than the second crystalline form of riboflavin also at temperatures above ambient temperature.

By using genetically modified microorganisms in the fermenter, recombinant DNA (rDNA) is present in the fermentation broth. Depending on the required specification of the final product, the recombinant DNA has to be fully removed or decomposed during the downstream and particularly during the purification steps. In the present description the term "DNA" includes any type of DNA (e.g. native or recombinant DNA) being included in the riboflavin crystals, being adsorbed at the surface of riboflavin crystals and being stabilized in contact with riboflavin crystals.

The content of DNA in the riboflavin product can be monitored by standard PCR (polymerase chain reaction). State of the art analytical tools based on PCR are used to detect defined sequences of rDNA (e.g. of a specific sequence of DNA of the production strain containing 200 base pairs). In comparison to chromatographic methods such as gas- or liquid chromatography, PCR is more sensitive by orders of magnitude. The detection limit depends on various parameters, e.g. on the number of cycles, the type of primer, the kind of polymerase, etc. Regarding rDNA of a defined sequence which is associated with crystalline riboflavin, the characteristic detection limit of the PCR is approximately 0.2 ppb. In a preferred embodiment of the process according to the invention the content of DNA having a defined length of base pairs (bp), preferably of 50 to 10000 bp, more preferably 100 to 1000 bp, most preferably of about 200 bp in the riboflavin crystals is reduced below the detection limit of approximately 0.2 ppb.

Conditions that decompose diluted DNA are known from the prior art. In the presence of an acid at a concentration of above $10^{-4}$ to $10^{-3}$ mol $l^{-1}$ diluted DNA is decomposed sufficiently fast at elevated temperature (cf. the dependence of the decomposition of DNA on the pH value is shown in Lindahl T. and Nyberg B.; Rate of Depurination of Native Deoxyribonucleic Acid; Biochemistry, 11, 19 (1972) 3610-3618). Citric acid at a concentration of about $10^{-3}$ mol $l^{-1}$ has been reported to decompose DNA at 60° C. within 1 hour (cf. Schriftenreihe des Fonds der Chemischen Industrie zu Förderung der Chemie und Biologischen Chemie im Verband der Chemischen Industrie e.V.; 60329 Frankfurt; Karlstrasse 21; Heft 32, Informationsband "Sicherheitsforschung in der Biotechnologie").

In a preferred embodiment of the process according to the invention the conditions in step (c) that decompose DNA are acidic conditions. Acidic conditions are preferably realized by the addition of an acid to the first crystalline form of riboflavin suspended in an aqueous slurry containing 0.5-50 wt.-%, preferably 2-10 wt.-% of riboflavin. In a preferred embodiment the acid is a mineral acid selected from the group consisting of sulfuric acid, nitric acid, phosphoric acid, hydrochloric acid, hydrobromic acid or an organic acid selected from the group consisting of acetic acid, formic acid and oxalic acid. The concentration of the acid in the aqueous slurry preferably should be higher than $10^{-4}$ mol $l^{-1}$, preferably between $10^{-4}$ and $10^{-1}$ mol $l^{-1}$, most preferably about 5 $10^{-4}$ mol $l^{-1}$. The pH value of the aqueous slurry should be preferably below 6, more preferably below 5 and most preferably below 4.

In another preferred embodiment of the process according to the invention the conditions in step (c) that decompose DNA are basic conditions. Basic conditions are preferably realized by the addition of a base to the first crystalline form of riboflavin suspended in an aqueous slurry containing 0.5-50 wt.-%, preferably 2-10 wt.-% of riboflavin. In a preferred embodiment the base is a mineral base selected from the group consisting of NaOH, KOH and $Ca(OH)_2$. The concentration of the base in the aqueous slurry preferably should be higher than $10^{-4}$ mol $l^{-1}$, preferably between $10^{-4}$ and $10^{-1}$ mol $l^{-1}$, most preferably about 5 $10^{-4}$ mol $l^{-1}$. The pH value of the aqueous slurry should be preferably above 8, more preferably above 9 and most preferably above 10.

In principle, when an aqueous solution containing DNA molecules is exposed to conditions that decompose DNA, the DNA strands are rapidly decomposed. However, if the DNA is not completely dissolved, e.g. if the DNA is adsorbed to a surface or included in the crystal grid (occlusion), the decomposition of the DNA is inhibited.

It has been reported that DNA can be adsorbed by and stabilized at surfaces. Studies were done to evaluate different carriers that adsorb DNA. A sufficient strong adsorption is needed to resist the attracting forces of the tip of an atomic force microscope. The nature and strength of the adsorption is dependent also on the presence of ions. In particular, divalent cations like $Mg^{2+}$ and $Ca^{2+}$ influence the stability (cf. Bezanilla et at.; Adsorption of DNA to Mica, Silylated Mica, and Minerals: Characterization by Atomic Force Microscopy; Langmuir 11 (1995) 655-659). Other studies revealed that DNA from *bacillus subtilis* adsorbed at surfaces can be stabilized to such an extent even resisting the attack of nucleases. The degree of stabilization is influenced by the composition of the surrounding solution, e.g. by the concentration of mono or divalent ions. A low pH value seems to have a stronger stabilizing effect (cf. Khanna M.; Yoder M.; Calamay L. and Stotzky G.; X-ray diffractometry and electron microscopy of DNA from *Bacillus subtilis* bound on clay minerals; Sciences of soils (1998) 3:1).

It has been surprisingly found that the decomposition of impurities of DNA, particularly of rDNA associated with crystals of riboflavin is strongly dependent on the nature of the crystalline form of riboflavin. While the decomposition of rDNA is particularly difficult in case that riboflavin anhydrate I is precipitated during the fermentation, the decomposition of rDNA in the downstream is relatively fast if riboflavin dihydrate is formed during the fermentation. Without the intention of being bound to any theory, it is assumed that rDNA, released from harvested cells is strongly associated with the riboflavin crystals.

The nature of the crystalline form of riboflavin drastically affects the efficacy of the purification process in the downstream, in particular the decomposition of recombinant DNA (rDNA) below the detection limit of analytical methods such as PCR. During the purification of the riboflavin, particularly the recombinant DNA associated with the riboflavin crystals can be decomposed rapidly when the crystal grid breaks up by transformation of the first crystalline form of riboflavin under the conditions of the purification. A new crystalline form of riboflavin, i.e. riboflavin dihydrate, was surprisingly found. Riboflavin dihydrate is formed preferably during the fermentation process and can be transformed during purification into a second crystalline form of riboflavin which is thermodynamically more stable at ambient temperature. The necessary data were established to control the formation of the desired crystalline form. In the prior art process the crystalline form does not change. Based on these findings a new and more efficient process for the purification of riboflavin was found, in particular with respect of the removal of recombinant DNA from the crystals.

In a preferred embodiment of the process according to the invention the first crystalline form of riboflavin which is precipitated in step (a) is riboflavin dihydrate. In step (b) the precipitated crystalline riboflavin dihydrate is isolated, preferably by decantation of the majority of the biomass, and optionally pasteurized. It has now been observed that when suspending the isolated crystalline riboflavin dihydrate in water and heating the slurry to a temperature of above 70° C., the viscosity significantly increases. The high viscosity can be lowered upon stirring at a high speed for a few minutes.

It can be verified by X-ray powder diffraction, that by said treatment crystalline riboflavin dihydrate is transformed into crystalline riboflavin anhydrate I. In addition, the crystal modification changes from short needles (10 to 20 μm) to long needles (50 to 200 μm). The formation of the long needles causes a significant increase in viscosity. A consequence of the transformation of crystalline riboflavin dihydrate in the suspension is the full disruption of the crystal grid which is immediately followed by a re-crystallization of the riboflavin molecules in the form of crystalline riboflavin anhydrate I. Impurities, in particular DNA, are liberated and fully released and diluted into the surrounding medium. In the presence of a small amount of acids (preferably at a pH value below 4) the DNA is rapidly decomposed at comparably low temperatures to an extent which is below the detection limit of conventional PCR; within 10 to 30 minutes at 50 to 70° C. and a pH value below 4, no DNA and particularly no rDNA can be detected in the riboflavin crystals.

In a preferred embodiment of the process according to the invention the transformation of the first crystalline form of riboflavin into the second crystalline form of riboflavin in step (c) is performed at increased temperature, preferably at a temperature of between 60° C. and 75° C., most preferably at about 70° C. Preferably, the transformation is performed under acidic conditions, most preferably at a pH value of below 4.

In a preferred embodiment of the process according to the invention, step (c) is performed at a temperature of between 60° C. and 75° C. using (i) a mineral acid, preferably $H_2SO_4$, $HNO_3$, HCl, HBr or $H_3PO_4$; or (ii) a base, preferably NaOH, KOH or $Ca(OH)_2$; or (iii) an organic acid, preferably formic acid, acetic acid, oxalic acid or citric acid.

In a preferred embodiment of the process according to the invention in step (c) an aqueous slurry containing the first crystalline form of riboflavin is transferred into a reactor equipped with an impeller stirrer. Then, preferably a sufficient amount of mineral acid or organic acid is added. The temperature is increased, preferably by means of a jacket, preferably to a temperature of between 60° C. and 75° C., most preferably of about 70° C. The stirring speed of the impeller stirrer is set to about 500 rpm. As soon as the viscosity raises, the stirring speed is increased, preferably up to about 2000 rpm to again liquefy the slurry. After ca. 20 min of treatment the slurry is filtered. The crystals obtained can be characterized by XRD and the content of rDNA can be analyzed by PCR.

Alternatively, after biomass separation and pasteurization the slurry containing the first crystalline form of riboflavin can be acidified and pumped constantly in a stirred multistage extractor. The residence time in the stirred multistage extractor, which is preferably 5 to 20 min, can be defined by the pumping rate. Preferably, the extractor can be heated to the desired temperature of about 70° C. by a jacket.

In a preferred embodiment of the process according to the invention, in step (c) the slurry containing the first crystalline form of riboflavin is preheated to about 70° C. by means of a heat exchanger before entering a stirred multistage extractor. The heat exchanger enables heating the slurry within seconds. The first crystalline form of riboflavin is preferably pumped continuously through the heat exchanger to rapidly achieve the desired temperature, and preferably further pumped trough a tube equipped by jacket heating and a multistage stirring system to apply sufficiently high shear forces. Instead of a stirred multi stage extractor, a reactor tube equipped with static mixers may also be used.

During the transformation the riboflavin crystals dissolve thereby liberating DNA molecules included or associated with the crystals. However, the dissolved riboflavin immediately re-crystallizes in the second crystalline form of riboflavin, which at ambient temperature (preferably 23° C. and higher) is thermodynamically more stable than the first crystalline form of riboflavin.

In contrast, when heating the corresponding fermentation liquid containing a slurry of riboflavin anhydrate I, no increase in viscosity is observed. The crystalline structure, determined by X-ray diffraction, does not change. Therefore, no transformation of the crystalline form is induced and riboflavin associated with DNA is not released into the solution. With respect to riboflavin anhydrate I, only the complete dilution of the slurry in a solvent or acidified water can liberate the DNA. Under these conditions, however, DNA can be decomposed below the PCR detection limit only by treating the riboflavin slurry at a temperature of above 95° C. for more than 12 hours, or above 100° C. for more than 6 hours, or above 120° C. for more than 2 hours, respectively.

In a preferred embodiment of the process according to the invention the first crystalline form of riboflavin is a riboflavin hydrate, preferably riboflavin dihydrate, and the second crystalline form of riboflavin is riboflavin anhydrate I. The precipitation of the first crystalline form of riboflavin in step (a) is preferably controlled by addition of seed crystals, more preferably by seed crystals of a riboflavin hydrate, most preferably by seed crystals of riboflavin monohydrate or seed crystals of riboflavin dihydrate.

In a preferred embodiment of the process according to the invention riboflavin dihydrate is precipitated in step (a) (first crystalline form of riboflavin) which then in step (c) is transformed into riboflavin anhydrate I (second crystalline form of riboflavin). In the course of the transformation, rDNA and other compounds that are associated with the riboflavin crystals are released into the surrounding medium. In the solution the dissolved rDNA can be easily decomposed by any suitable condition or ingredient, e.g. by a mineral acid or an organic acid that decomposes dissolved DNA.

In step (d) of the process according to the invention the second crystalline form of riboflavin is isolated. Preferably the second crystalline form of riboflavin is isolated by filtration, centrifugation or decantation. The crystals obtained from step (d) are preferably washed with cold ethanol or a mixture of ethanol and water and then dried.

The invention relates to an efficient process for the purification and crystallization of riboflavin in which (recombinant) DNA is decomposed below the detection limit of conventional PCR. In a preferred embodiment the process comprises the formation and sterilization of suitable seed crystals, preferably seed crystals of riboflavin monohydrate or riboflavin dihydrate. In a preferred embodiment the precipitation of a first crystalline form of riboflavin, preferably riboflavin dihydrate, is initiated by means of said seed crystals in the fermenter. Furthermore, the process comprises the removal of DNA molecules associated with the first crystalline form of riboflavin by transforming the first crystalline form of riboflavin, preferably riboflavin dihydrate, into a second crystalline form of riboflavin, preferably riboflavin anhydrate I, under conditions that decompose diluted DNA. Preferably the transformation of the first crystalline form of riboflavin into the second crystalline form of riboflavin is performed by heating the suspended first crystalline form of riboflavin in the presence of an acid. The concentration of the acid is preferably above $10^{-4}$ mol $l^{-1}$, the pH value of the solution is preferably below 6, more preferably below 5 and most preferably below 4.

The individual crystalline forms of riboflavin, in particular riboflavin anhydrate II, riboflavin anhydrate III, riboflavin dihydrate and riboflavin tetrahydrate can be used in the field of human and animal nutrition and animal health and human health.

The following examples further illustrate the process according to the invention.

EXAMPLE 1

Characterization by DVS and X-Ray Diffraction

Figure 3:
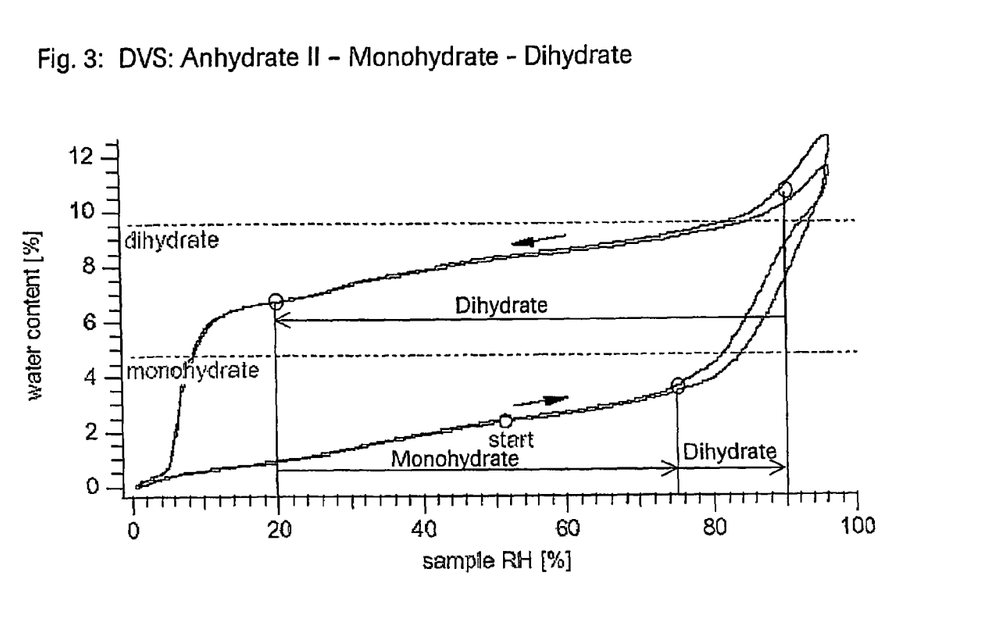
FIG. 3 illustrates the Dynamic Vapor Sorption (DVS) of riboflavin Anhydrate II, Monohydrate and Dihydrate.

A sample of modification B/C (as described in EP-A 995 749; corresponding to riboflavin monohydrate) was investigated by combined DVS—gravimetry and combined DVS—x-ray diffraction, FIG. 3. The sample was fixed at ambient temperature and at 52% relative humidity (water vapor). In both combined methods, the relative humidity (RH) was constantly increased until a relative humidity of about 96% was reached. Then, the relative humidity was constantly decreased to 0%. Then, the humidity was increased up to 52% again to reach the starting point. The cycle was repeated a second time.

The uptake and the release of crystalline bound water in the cycle depending on increasing or decreasing water vapor followed a hysteresis. The hysteresis can be explained by the kinetically determined uptake during increasing relative humidity and the retarded release of crystal water during decreasing relative humidity.

The theoretical amount of water incorporated in the crystalline forms of riboflavin that leads to the different hydrates is listed below:

From riboflavin anhydrate to riboflavin monohydrate: 4.79 wt.-%

From riboflavin anhydrate to riboflavin dihydrate: 9.57 wt.-%

From riboflavin anhydrate to riboflavin trihydrate: 14.36 wt.-%

From riboflavin anhydrate to riboflavin tetrahydrate: 19.15 wt.-%

Parallel scanned X-ray diffraction showed at least three clearly distinguishable spectra for crystalline forms that appeared at different ranges of relative humidity:

| Ranges | Crystalline form |
| --- | --- |
| 0% RH | riboflavin anhydrate II |
| 20 < RH < 75% | riboflavin monohydrate |
| 90–20% | riboflavin dihydrate |

Riboflavin anhydrate II shows a X-ray diffractogram differing from that of riboflavin anhydrate I. Therefore, it can be identified as a real polymorph of riboflavin anhydrate I. By increasing the relative humidity the crystalline structure changes to the form of riboflavin monohydrate. At a relative humidity close to 20% the structure of riboflavin monohydrate is still established. Like in an almost dry sponge, only a few positions in the grid of the riboflavin crystal are occupied by water molecules. The positions are filled by increasing the relative humidity. Above about 75% relative humidity, the crystal structure suddenly changes again to the structure of riboflavin dihydrate, before the theoretical quantity of water for riboflavin monohydrate has been taken up. Above a relative humidity of 75%, the water is incorporated rapidly into the structure of riboflavin dihydrate. At a relative humidity of about 92% the water uptake reaches a theoretical amount of 9.57 wt.-% which corresponds to riboflavin dihydrate.

Water is released constantly by decreasing the relative humidity. The structure of riboflavin dihydrate remains intact until a relative humidity of 20% is reached. At a relative humidity of 20% the dihydrate structure contains still about 1.3 mol water per mol riboflavin. Then, the structure changes directly to riboflavin anhydrate II.

The three different forms can be clearly distinguished by Raman spectroscopy.

Figure 4:
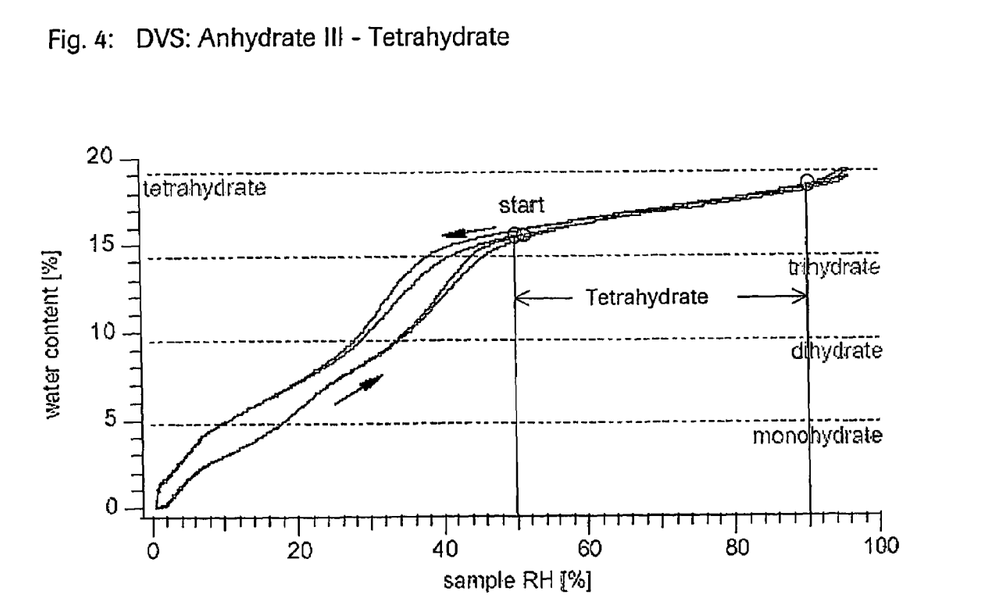
FIG. 4 illustrates the Dynamic Vapor Sorption (DVS) of riboflavin Anhydrate III and tetrahydrate.

A second sample of a crystalline form of riboflavin was analyzed by DVS, FIG. 4, in the same way the sample "B/C" was analyzed. The sample showed a crystalline structure that could be identified as type C, according to U.S. Pat. No. 2,603,633.

Two different crystalline forms could be identified in the ranges of:

| ranges | crystalline form |
| --- | --- |
| 0% < RH | riboflavin anhydrate III |
| 50% < RH < 90% | riboflavin tetrahydrate |

The structure of riboflavin tetrahydrate is known as type C (modification). Riboflavin anhydrate III is a new crystalline form and is the third anhydrous modification besides riboflavin anhydrate I and riboflavin anhydrate II. Its X-ray diffractogram differs from all the other diffractograms of the crystalline forms of riboflavin.

EXAMPLE 2

Methods to Determine the Solubilities and Supersaturations

The experiments were conducted in a heat flow calorimeter. The process of dilution by heating and crystallisation by cooling was monitored by a turbidity sensor. 36 mg of crystals of riboflavin anhydrate I or 60 mg of crystalline form of riboflavin monohydrate or 120 mg of crystals of riboflavin dihydrate, respectively, were suspended in the fermentation solution and heated to 80° C. at a rate of 0.1° C. per minute. The temperature was held during 60 min. Then the system was cooled again to 20° C. at a rate of 0.1° C./min.

At 39° C. the dependence of the supersaturation line is only a weak function of the temperature. Therefore, another method (MethB) was applied to determine the supersaturation at 39° C.: 420 mg of crystals of riboflavin tetrahydrate were suspended and fully dissolved by heating to 69° C. The concentration of riboflavin was 0.6 mg ml$^{-1}$. After cooling again to 39° C., the temperature was kept constant. After 3 hours, the crystallisation started slowly (cf. FIG. 2).

The same experiment performed with 360 mg of crystals of riboflavin tetrahydrate (corresponding to 0.7 mg ml$^{-1}$) led to spontaneous crystallisation still at 46° C.

It can thus be concluded that at 39° C. the supersaturation line is below 0.6 mg ml$^{-1}$.

EXAMPLE 3

Preparation of the Seed Crystals, Sterilization and Vaccination 500 mg of crystals of riboflavin monohydrate were sterilized at 140° C. for 50 min in an oven, suspended in 5 ml ethanol for 10-200 min, preferably 20-40 min and prior induction 10 ml sterile $H_2O$ were added for better handling of the liquid. The suspension was added to the bioreactor after 6 h by a sterile bottle with needle. Crystals of riboflavin dihydrate were formed and in the culture remained monoseptic. From these experiments, it can be concluded that it is possible to direct the crystal modification to riboflavin dihydrate.

Measurement of the soluble fraction of riboflavin in induced and uninduced cultures showed major differences: in the uninduced culture an oversaturated solution was obtained after 6-9 h. Then the solubility decreases significantly within 1 h. In case of the induced cultures this phenomenon is not observed. The solubility of riboflavin (approximately 0.4 gl$^{-1}$) is not exceeded. It is controlled by x-ray diffraction whether the crystalline form of the crystals changes during the sterilization procedure.

EXAMPLE 4

Removal of DNA from the Riboflavin Crystals of Riboflavin Dihydrate by a Batch Operation After sterilization and decantation of the major part of the biomass the remaining riboflavin slurry that contains 6 wt.-% of riboflavin crystals is treated by adding a mineral acid, preferably sulfuric acid, nitric acid, phosphoric acid and/or organic acid, preferably acetic acid, formic acid, oxalic acid. After adding the acid the concentration of the acid in the slurry was 5 10$^{-4}$ mol l$^{-1}$. The acidified slurry was stirred intensively.

Figure 5:
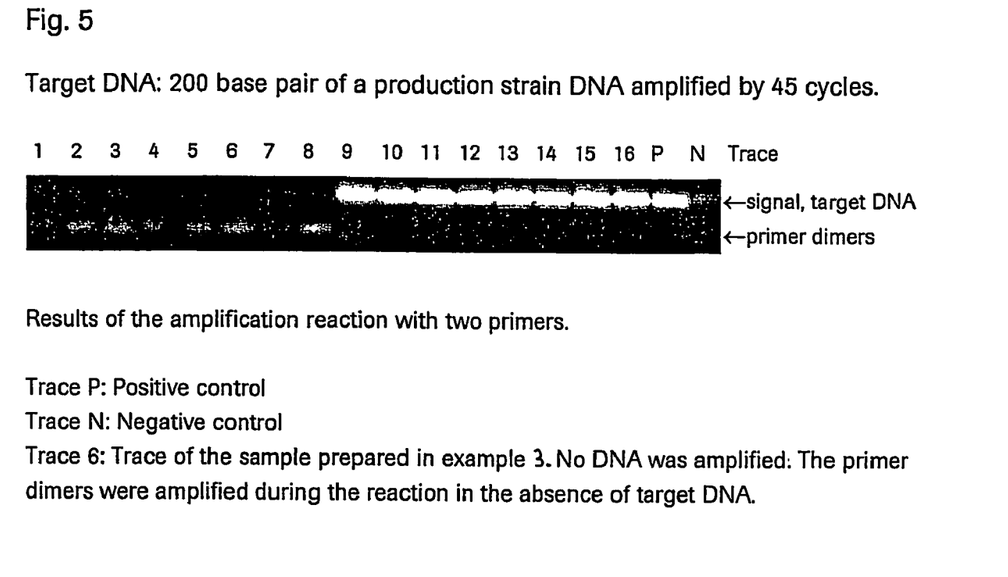
FIG. 5 illustrates the agarose gel electrophoresis analysis of the target DNA amplified with two primers by PCR.

The slurry was filled in a 1.5 liter reactor with a impeller stirrer. The slurry was acidified and the temperature was increased by jacket temperature up to 70° C. The stirring speed was set to 500 rpm. As soon as the viscosity raised, the stirring speed was increased up to 2000 rpm to again liquefy the slurry. After the treatment of 20 min the slurry was filtered off. The crystals obtained were characterized by XRD. The content of rDNA was analyzed by PCR (cf. FIG. 5).

EXAMPLE 5

Removal of DNA from the Riboflavin Crystals of Riboflavin Dihydrate by a Continuous Operation The slurry after biomass separation and pasteurization according to Example 4 was acidified and pumped constantly in a stirred multistage extractor. The residence time 5 to 20 min in the stirred multistage extractor was defined by the pumping rate. The extractor could be heated by a jacket to the desired temperature of 70° C.

In a different experiment, the slurry was preheated to 70° C. by a heat exchanger before entering in the stirred multistage extractor. With a heat exchanger the slurry could be heated within seconds. Instead of an stirred multi stage extractor, a reactor tube equipped with static mixers was used.

EXAMPLE 6

A process for the preparation of riboflavin tetrahydrate is described in U.S. Pat. No. 2,603,633. The process basically uses a solvent to rapidly precipitate the riboflavin in order to obtain the desired tetrahydrate "type C" (modification). The samples prepared by this method transform at a relative humidity of 95% in about 100 min into riboflavin dihydrate.

Another process for the manufacture of riboflavin tetrahydrate in small quantities is based on evaporation of an aqueous solution. A procedure is described below:

500 mg of riboflavin (assay>98 wt.-%, from chemical manufacturing) were dissolved in 7 liters of de-ionized water. The solution was then filtered over a Sartorius filter system consisting of a glass fiber filter and a 5μ Teflon filter. The filtered solution was then evaporated in a Büchi rotating flask evaporator system. At a vacuum of 20-25 mbar and a bath temperature of maximal 40° C. the solution was constantly sucked into the evaporation flask. Simultaneously, water was evaporated. The volume of the flask was kept at maximal 200 ml. The crystallization started at the end of the procedure.

Finally, all the 7 liters were sucked into the evaporator flask and evaporated. The volume in the evaporator flask was reduced by evaporation to about 100 ml. The suspension was then filtered, without additional washing and dried at high vacuum, p<0.05 mbar at max. 35° C. The sample was then characterized by x-ray diffraction to confirm the tetrahydrate structure. The sample was then used for further experiments.

EXAMPLE 7

Control DNA

The entire genome of the production strain was used as a positive control of the PCR amplification. The concentration of the genome was used up to 100 ng $\mu l^{-1}$.

PCR Amplification

Two primers were used. With the primers a 200 base pair (bp) fragment was amplified, if a sample contained DNA of a production strain in a concentration higher than 0.2 parts per billion (ppb).

PCR-Program
  initial denaturation
  45 cycles of: 40 seconds at 94° C.
    60 seconds at 55° C.
    60 seconds at 72° C.
  Finally, the sample was kept for 600 seconds at 72° C.

Extraction

To 50 mg of riboflavin, 0.5 ml TE-buffer (pH 8) with 1% desoxycholate were added. After 10 minutes of shaking, 0.7 ml of phenol (saturated with TE) were added and shacked again for 15 min. After the phase separation, 50 μl of the aqueous phase were purified by chromatography (MicroSpin S200, Amersham Pharmacia Biotech) to remove rests of phenol, desoxycholate and riboflavin.

Identification

The amplified products were identified by agarose gel electrophoresis using an UV active nucleic acid strain to mark the DNA.

The invention claimed is:

1. Process for the purification of fermentatively produced riboflavin that has at least one impurity which is a DNA comprising the steps of:
   (a) precipitating a first crystalline form of fermentatively produced riboflavin,
   (b) isolating the first crystalline form of riboflavin,
   (c) transforming the first crystalline form of riboflavin into a second crystalline form of riboflavin under conditions that decompose diluted DNA, and
   (d) isolating the second crystalline form of riboflavin,
   wherein the first crystalline form of riboflavin is a riboflavin dihydrate and the amount of DNA in the riboflavin crystals of step (d) is below about 0.2 parts per billion.

2. Process according to claim 1, characterized in that after step (b) the process further comprises the step of pasteurizing the first crystalline form of riboflavin before transforming the first crystalline form in step (c).

3. Process according to claim 1, characterized in that the second crystalline form of riboflavin is riboflavin anhydrate 1.

4. Process according to claim 1, characterized in that in step (c) the conditions that decompose diluted DNA are acidic or basic conditions.

5. Process according to claim 4, characterized in that the acidic conditions are caused by an acid having a concentration of between $10^{-4}$ and $10^{-1}$ $mol^{-1}$.

6. Process according to claim 1, characterized in that in step (a) the precipitation of the first crystalline form of riboflavin is induced by addition of seed crystals to the fermentatively produced riboflavin.

7. Process according to claim 6, characterized in that the seed crystals comprise seed crystals of a riboflavin hydrate.

8. Process according to claim 7, characterized in that the seed crystals of the riboflavin hydrate are seed crystals of riboflavin dihydrate or seed crystals of riboflavin monohydrate.

9. Process according to claim 1, characterized in that step (c) is performed at a temperature of between 60° C. and 75° C. using
   (i) a mineral acid,
   (ii) a base, or
   (iii) an organic acid.

10. Process according to claim 1, characterized in that in step (c) a slurry comprising the first crystalline form of riboflavin is pumped continuously through a heat exchanger and further pumped through a tube equipped with a jacket heating and either a multistage stirring system or static mixers.

11. Process according to claim 2, characterized in that in step (c) the conditions that decompose diluted DNA are acidic or basic conditions.

* * * * *